United States Patent [19]
Paavola et al.

[11] 4,068,654
[45] Jan. 17, 1978

[54] BLOOD PRESSURE MEASURING APPARATUS AND METHOD

[75] Inventors: Oiva A. Paavola; Richard D. Brugger, both of Erie, Pa.

[73] Assignee: Oiva A. Paavola, Erie, Pa.

[21] Appl. No.: 658,178

[22] Filed: Feb. 17, 1976

Related U.S. Application Data

[63] Continuation-in-part of Ser. No. 551,071, Feb. 19, 1975, abandoned, which is a continuation-in-part of Ser. No. 344,752, March 26, 1973, abandoned.

[51] Int. Cl.$^2$ .............................................. A61B 5/02
[52] U.S. Cl. .............................................. 128/2.05 N
[58] Field of Search ............... 128/2.05 T, 2.05 N, 128/2.05 V, 2.05 R, 2.05 M, 2.06 F

[56] References Cited
U.S. PATENT DOCUMENTS

| | | | |
|---|---|---|---|
| 1,802,685 | 4/1931 | Trier | 128/2.05 N |
| 1,900,285 | 3/1933 | Huber | 128/2.05 N |
| 3,123,068 | 3/1964 | Bigliano | 128/2.05 N |
| 3,230,950 | 1/1966 | Buffington | 128/2.05 R |
| 3,572,316 | 3/1971 | Vogelman et al. | 128/2.05 R |
| 3,742,937 | 7/1973 | Manuel et al. | 128/2.05 T |
| 3,773,038 | 11/1973 | Smith et al. | 128/2.06 F |
| 3,807,388 | 4/1974 | Orr et al. | 128/2.05 P X |
| 3,814,083 | 6/1974 | Fletcher et al. | 128/2.05 A |
| 3,930,494 | 1/1976 | Maurer et al. | 128/2.05 A |

FOREIGN PATENT DOCUMENTS

| | | | |
|---|---|---|---|
| 509,637 | 10/1930 | Germany | 128/2.05 N |
| 469,703 | 12/1928 | Germany | 128/2.05 N |

*Primary Examiner*—Kyle L. Howell

[57] ABSTRACT

An instrument for measuring blood pressure by sensing the Korotkoff sounds which prevail only between the systolic and the diastolic points. The instrument used is essentially a hand held device which is held in direct contact with the skin over an artery. The instrument has a pressure-sensitive element which responds to pressure, and a crystal transducer which responds to Korotkoff sounds. A pressure is exerted on the instrument occluding the artery and stopping the Korotkoff sounds, and, as the pressure is reduced and the Korotkoff sounds commence, the crystal transducer senses the vibrations from the artery which vibrations are Korotkoff sounds. The crystal triggers a memory circuit, the contents of which are shown on the digital display. The digital display shows the pressure sensed by the strain gauge at the time the sounds appear at the systolic point and again at the diastolic point.

5 Claims, 6 Drawing Figures

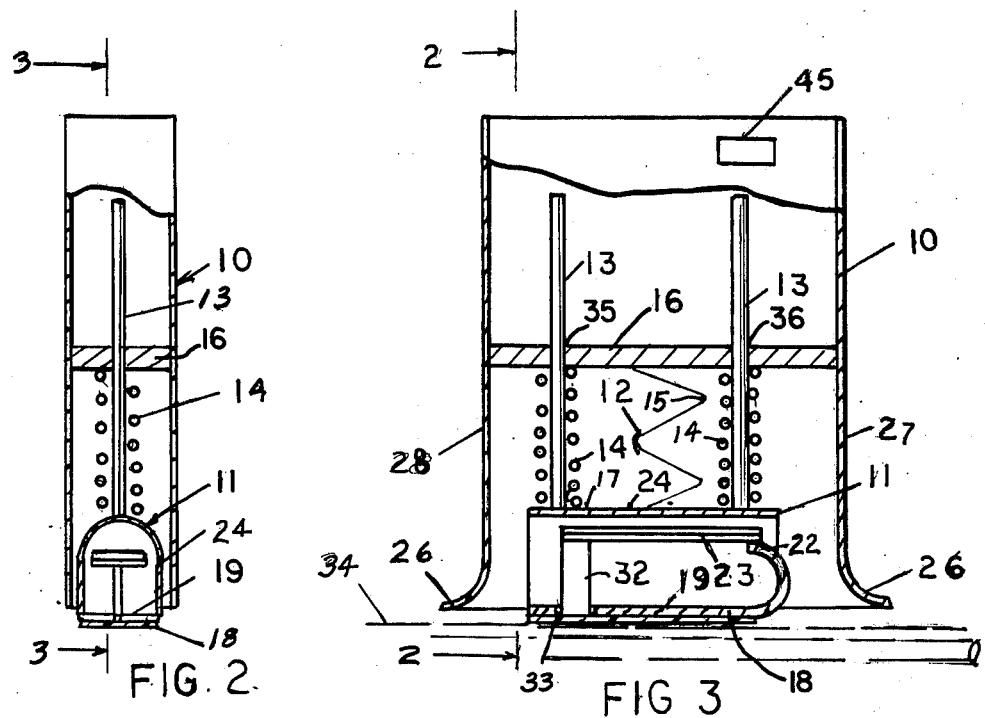
FIG. 2
FIG 3
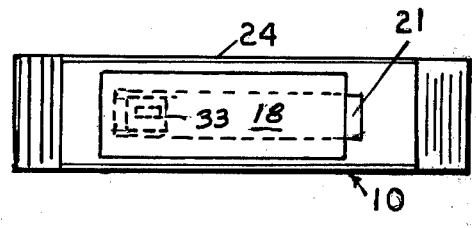
FIG 4
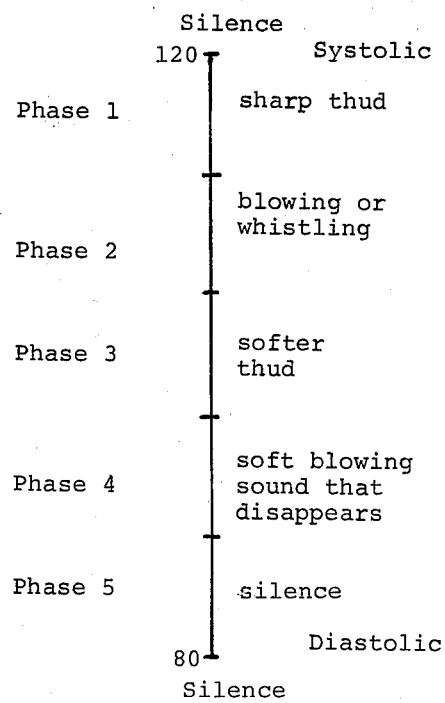
FIG. 5

BLOOD PRESSURE MEASURING APPARATUS AND METHOD

REFERENCE TO PRIOR APPLICATIONS

This application is a continuation-in-part of Application Ser.No. 551,071, filed Feb. 19, 1975, which in turn is a continuation-in-part of Application Ser.No. 344,752 filed Mar. 26, 1973, both now abandoned.

REFERENCE TO PRIOR ART

U.S. Pat. No. 3,773,038 shows a digital computing cardiotachometer for measuring heart rate using a transducer and an oscillator which actuate a display. U.S. Pat. No. 3,230,950 shows an apparatus and method for determining blood pressure using a cuff and a separate transducer to actuate a display device. Applicant uses a Korotkoff-sound-sensitive transducer in combination with a pressure-sensitive pickup operating through an electronic circuit actuating a digital readout. U.S. Pat. No. 3,807,388 shows a heartbeat rate monitor using an oscillator in combination with a display.

GENERAL DESCRIPTION OF THE INVENTION

The system described herein provides a pressure pad to be placed over an artery and to which sufficient pressure is exerted to occlude the artery. As the force applied to this pad is gradually reduced and Korotkoff sounds commence, the pressure, expressed in millimeters of mercury, is displayed. A local pressure region is engaged by a transducer device with a pressure pad in place of the traditional cuff.

The Korotkoff sounds are the sounds by which the arterial pressure is determined. These sounds are heard outside the artery and distal to the devise that is occluding the artery and vary in character as the pressure on the device is reduced to the diastolic point where the sounds stop. The sounds are divided into phases, as indicated in FIG. 5. Phase one is characterized by clear tapping or thumping sounds. Phase one ends, and phase two begins when the sounds appear as a blowing or swishing sound. In phase three, a softer thud than in phase one appears; and, in phase four, a soft blowing sound, which disappears at the second distolic point, appears. The second diastolic point is the diastolic point referred to in this application. Above the systolic point, there is silence and, below the second diastolic point, there is silence and, as indicated typically, the systolic point might appear at 120 millimeters of mercury and the diastolic point at 80 millimeters of mercury. In such an example, the patient's blood pressure would be 120 over 80.

OBJECTS OF THE INVENTION

It is an object of the invention to provide an improved device for indicating blood pressure.

Another object of the invention is to provide a device for indicating blood pressure which is simple in construction, economical to manufacture, and simple and efficient to use.

Another object of the invention is to provide a blood pressure measuring device wherein a crystal senses Korotkoff sounds and the pressure is sensed by a strain gauge. Information from the crystal and the strain gauge are converted to a digital reading of the applied pressure at each heart beat between the limits of the systolic and diastolic pressures.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

GENERAL DESCRIPTION OF THE DRAWINGS

FIG. 2 is a cross-sectional view on line 2—2 of FIG. 3.

FIG. 3 is a cross-sectional view on line 3—3 of FIG. 2.

FIG. 4 is a bottom view of the instrument.

FIG. 5 is a diagram showing the phases of Korotkoff sounds.

DETAILED DESCRIPTION OF THE DRAWINGS

Figure 1:
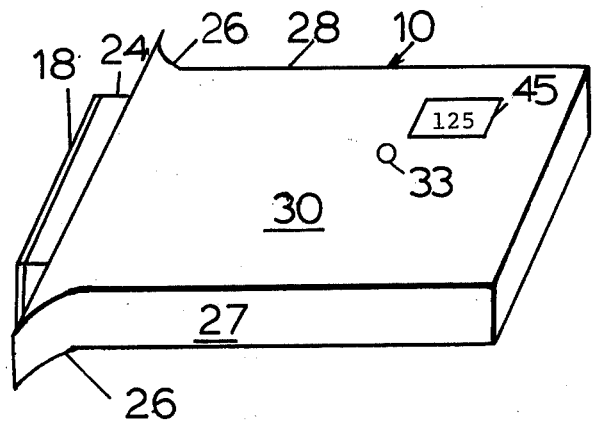
FIG. 1 is an isometric view of the blood pressure measuring device according to the invention.

Now, with more particular reference to the drawings, the physical unit 10 shown in FIG. 1 is generally rectangular in shape and could be approximately 6 inches long and 1½ inches high and ½ inch thick. Projecting from one end is the detector head with the rubber sheet 18 extending therefrom and flanges 26 integrally fixed to the sides of the body provide finger rests so that the physician can grasp the side edges 27 and 28 between the thumb and forefinger of one hand. A window 45 is provided in the upper surface to display a digital readout.

A detector head as shown in FIGS. 2 and 3. The detector head 11 has a strain gauge 12 for sensing pressure exerted on the rubber sheet 18 by the hand of the person holding the instrument 10. Crystal 23 is connected to rubber pad 18 and it senses Korotkoff sounds in the circulatory system. The detector head 11 has an enclosing channel 24 which rests on the metal plate 19. The metal plate 19 has an upwardly curving end 21 which forms an arm and is attached at 22 to the piesoelectric crystal bymorf 23.

The amplifier, crystal and signal conditioner act as a filter which filters out sounds that are not conventionally considered Korotkoff sounds, where Korotkoff sounds are those traditionally observed by a trained physician. The rear end of the crystal bimorph 23 is cemented to the arm 32 which, in turn, is cemented to the rubber sheet 18 and which passes through the notch 33 in the plate 19. The crystal bimorph provides electrical output as it is vibrated by Korotkoff sounds.

The rubber sheet 18 may rest on the skin indicated at 34. Guide rails 13 are fixed to the upper side of channel 24 and the plate 16 is slidably supported on the rails which pass through holes 35 and 36. Compression springs 14 rest between the channel 24 and the plate 16 and urge it upward and transmit force from the hand holding the instrument to the skin. A flexible member 15 supports the strain gauge 12. The flexible member 15 is attached to the channel 24 at its lower end, to plate 16 at its upper end, and is supported generally in an M shape. The change in the resistance of the strain gauge 12 is a measure of the pressure applied to the skin by a force exerted on instrument 10 by the hand of the operator which is transmitted through the springs 14 to the channel 11 and the plate 19 and flexible sheet 18.

Figure 6:
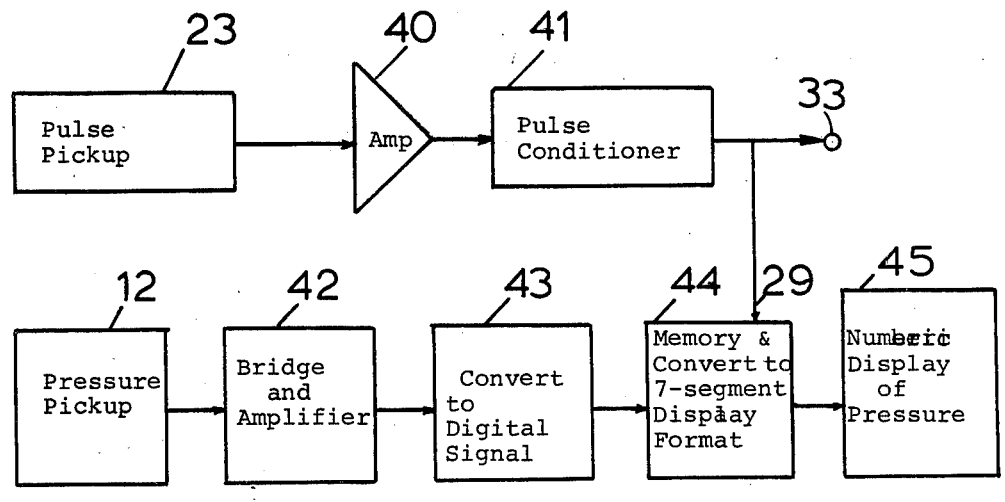
FIG. 6 is a block diagram view of the electronic circuit of the invention.

The circuit shown in FIG. 6 shows a first circuit which includes the sound pickup 23, audible frequency range amplifier 40 and signal conditioner 41 which converts the sound signal to a digital pulse and connects to the memory and converts to seven segment display format 44. The second circuit includes the pressure pickup strain gauge 12 which feeds through the bridge and amplifier 42 to the convert-to-digital signal 43, memory 44 and digital display 45. Signal conditioner 41 causes light 33 to flash, indicating that Korotkoff sounds are being detected, and the numeric display will show the pressure at the particular time. The sound signal from crystal bimorph 23 is fed through a connection into the memory and converter unit 44 to the displays 70, 71 and 72.

The sound signal from the pulse pickup 23 is amplified. Thereafter, the electrical signal is used for two purposes: (1) to cause an LED (light emitting diode) connected to 33 to flash at each pulse; and (2) to trigger the numeric display circuitry to show the current reading of pressure by means of 29.

In appearance, the instrument is a rectangular box as shown in FIG. 1, with the detector head 11 protruding from one end. The instrument is suitable to be carried in a shirt or coat pocket. Various other shapes and configurations of the device are possible, depending upon the specific application and the extent to which the electronic circuitry is to be miniaturized.

To use the device, the operator grasps the instrument with his thumb and index finger, placing the finger tips against the finger flanges 26. The instrument then assumes a position much like a pencil used for writing, resting againgst the hand in the same manner. The operator lines the instrument up with an artery where the pulse pickup in the instrument is downstream from the heart. The operator then applies some pressure directly onto the skin over the artery, or wherever he is planning to measure blood pressure. If he is measuring over an artery, he will observe that the pulse light flashes and the numerical indicator flashes numbers.

The operator applies increased pressure slowly until the flashing stops. He reads the numerical indicator. For example, it may read 125. He then decreases the pressure slightly and slowly and observes that the indicator and pulse light begin to flash again. It will continue to flash decreasing numbers as the pressure decreases. He continues to decrease slowly until the flashing stops. He then reads the numerical indicator. For example, it may read 82. The blood pressure is then 125/82 for this example.

There is a problem in sensing the precise systolic point and the precise diastolic point in blood pressure measurements because a certain amount of discretion is required to detect these particular points. Part of the problem is the subjective evaluation of the sound by the physician using conventional equipment, and another part of the problem is the noise environment of the signal. A discussion of detecting signals and noise appear in the article by Richard D. Brugger in Computer Design, November 1970, at pages 115-120. The problem results from the fact that the signal at the systolic point are large enough to be resolved from the high noise level if the detection criteria is set high enough; but such a high threshold would not permit detection of the small signal at diastolic. At diastolic pressure, the signal is small, but the noise is still smaller. It thus seems logical to either vary the threshold or vary the gain of the amplifier according to the applied pressure, as observed by the strain gauge. From the signal processing point of view, it is better to vary the amplifier gain.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which exclusive property or privilege is claimed are defined as follows:

1. An instrument for evaluating the circulatory system of an animal by sensing externally applied pressure and by sensing Korotkoff sounds at the systolic and diastolic points comprising,
    a body having finger-engaging means thereon,
    a detector head supported on said body,
    said detector head having skin-engaging means thereon,
    a pressure pickup means and a sound-pickup means connected to said skin-engaging means,
    a first circuit,
    and a second circuit,
    said first circuit comprising,
    said pressure pickup means and,
    a memory means connected to said pressure pickup means,
    and a digital numeric display means connected to said memory means,
    said second circuit comprising,
    said sound pickup means,
    means connecting said sound pickup means to said memory means for triggering said memory means to actuate said numeric display means whereby said numeric display means indicates proportional to the pressure exerted on said pressure pickup means at the occurance of each said sound by said pickup.

2. The instrument recited in claim 1 wherein said first circuit further comprises a memory and said second circuit means comprises an audio range amplifier connected to said sound sensing means and a signal conditioner connected to said amplifier and to said memory.

3. The instrument recited in claim 2 wherein said first circuit comprises a bridge amplifier conncected to said pressure sensing means, a convert-to-signal circuit connected to said bridge amplifier and said memory connected to said signal conditioner further connected to said numeric display and to said convert-to-signal circuit.

4. The instrument recited in claim 1 wherein said instrument includes memory means connected to said readout means whereby said display is retained until the occurence of a second Korotkoff sound after a first Korotkoff sound.

5. A method of measuring blood pressure in an artery comprising,
    providing a hand-held instrument having a body having finger-engaging means thereon including a pressure- pickup device connected to Korotkoff sound-pickup means and to a digital readout device supported on said body,
    manually exerting a pressure through said hand-held instrument on skin over said artery, said pressure being sufficient to occlude said artery and being exerted through said pressure-pickup device, reducing said manually exerted pressure on said pressure-pickup device gradually until Korotoff sounds develop in said artery, observing the pressure indicated by said digital read-out device at which said Korotoff sounds appear at the systolic point, reducing said manually exerted pressure on said pressure-pickup device gradually until said Korotkoff sounds substantially disappear at the diastolic point and observing the pressure indicated by said read-out device at which said sounds substantially disappear.

* * * * *